United States Patent [19]

Bonfield et al.

[11] Patent Number: 5,470,803

[45] Date of Patent: Nov. 28, 1995

[54] METHOD FOR THE PREPARATION OF CARBONATED HYDROXYAPATITE COMPOSITIONS

[75] Inventors: William Bonfield, Welwyn; Serena M. Best, Ridgmont; Jake E. Barralet, Bristol, all of United Kingdom

[73] Assignee: Queen Mary and Westfield College, London, United Kingdom

[21] Appl. No.: 245,679

[22] Filed: May 18, 1994

[30] Foreign Application Priority Data

May 19, 1993 [GB] United Kingdom .................. 9310321

[51] Int. Cl.⁶ ................................................. C04B 35/00
[52] U.S. Cl. ............................ 501/1; 423/308; 423/311
[58] Field of Search ................................ 501/1; 423/308, 423/311

[56] References Cited

U.S. PATENT DOCUMENTS

| | | | |
|---|---|---|---|
| 4,503,157 | 3/1985 | Hatahira | 501/1 |
| 4,917,702 | 4/1990 | Scheicher et al. | 501/1 |
| 4,919,751 | 4/1990 | Sumita et al. | 501/1 |

OTHER PUBLICATIONS

Ellies, L. G.; Nelson, D. G. A.; Featherstone, J. D. B., "Crystallographic Structure and Surface Morphology of Sintered Carbonated Apatites," *Journal of Biomedical Materials Research*, vol. 22, (Jun. 6, 1988), pp. 541–553.

Nelson et al. "Preparation, Analysis, and Characterization of Carbonated Apatites," Calcified Tissue International (1982) 34:S69–S81, (no month available).

Nordstrom et al. "Carbonate–Doped Hydroxyapatite," Journal of Materials Science: Materials in Medicine 1 (1990), pp. 182–184, (no month available).

*Primary Examiner*—Wayne Langel
*Attorney, Agent, or Firm*—Fitch, Even, Tabin & Flannery

[57] ABSTRACT

A method for the preparation of a carbonated hydroxyapatite composition which has a density of at least 95% of the theoretical density, which method comprises sintering at substantially atmosphere pressure a green carbonated hydroxyapatite composition containing up to 20% by weight of $CO_3^{2-}$ ions and having a green density of from 25 to 60% of the theoretical density at a temperature in the range of from 750° to 1450° C. in carbon dioxide containing from 0.001 to 0.10 grams of water per liter of gas, the sintering temperature being selected within the above range and the green composition being sintered for a period of time sufficient to cause the green composition to densify to at least 95% of the theoretical density.

14 Claims, 2 Drawing Sheets

METHOD FOR THE PREPARATION OF CARBONATED HYDROXYAPATITE COMPOSITIONS

The present invention relates to a method for forming a carbonated hydroxyapatite composition and, in particular, to a method for forming translucent carbonated hydroxyapatite compositions which are substantially fully dense.

Hydroxyapatite is a member of the apatite group of minerals and has the chemical formula $Ca_{10}(PO_4)_6(OH)_2$. It is, essentially, a calcium phosphate including hydroxide having a Ca/P ratio of 1.67.

Synthetic hydroxyapatite $Ca_{10}(PO_4)_6(OH)_2$ has been reported as having been used as a bone replacement material in porous, granular, plasma sprayed and dense forms. Investigations have shown hydroxyapatite to be similar structurally to bone material. However hydroxyapatite is one of the range of stoichiometric calcium phosphate apatites. Human and animal bone mineral have been shown to contain significant amounts of carbonate. There is evidence that the carbonate group can substitute in two sites, the phosphate and hydroxyl sites, termed B and A respectively; bone mineral being predominantly a B type apatite. Despite being closer to bone mineral structurally, there has been no previous major application in the biomedical field of carbonated apatites.

Synthetic B type apatite is produced by a precipitation method by the mixing of calcium, phosphate and carbonate ions in a highly basic environment. This method can result in a range of apatite crystal morphologies and sizes, depending upon the concentration of the various ions and solution temperature.

There are two main stages in processing the precipitated apatite into a dense ceramic, namely the production of a green body and sintering. Green or unfired compacts are produced by two main methods, slip casting and the pressing of a powder in a mould, which normally results in a body with from 40 to 60% porosity. Sintering is the densification of the green compact on heating, normally at temperatures >0.5 Tm, as a result of diffusion processes, with the driving force being the reduction in surface area. Apatites are thought to densify by bulk and grain boundary diffusion mechanisms. Grain growth is a process that occurs simultaneously and after densification. Usually in order to optimize properties, such as hardness and fracture toughness, it is desirable to maximise the density and minimize the grain size. However, as grain growth often occurs during densification, intergranular porosity can be formed as the grain boundaries migrate past regions of porosity. Grain growth is often more energetically favourable than the removal of this porosity. Hence 100% dense apatites have not been produced heretofore by sintering alone. An external isotatic pressure can be applied during sintering to promote complete densification, this process being termed hot isostatic pressing.

We have now developed a method for the preparation of substantially fully dense carbonated hydroxyapatite compositions which does not involve hot isostatic pressing and which produces translucent compositions.

Accordingly, the present invention provides a method for the preparation of a carbonated hydroxyapatite composition which has a density of at least 95% of the theoretical density, which method comprises sintering at substantially atmosphere pressure a green carbonated hydroxyapatite composition containing up to 20% by weight of $CO_3^{2-}$ ions and having a green density of from 25 to 60% of the theoretical density at a temperature in the range of from 750° to 1450° C. in carbon dioxide containing from 0.001 to 0.10 grams of water per liter of gas, the sintering temperature being selected within the above range and the green composition being sintered for a period of time sufficient to cause the green composition to densify to at least 95% of the theoretical density.

The temperature at which a densified hydroxyapatite composition having a density of at least 95% of the theoretical density and preferably having a density of from 98% to 100% of the theoretical density is obtained on sintering a green carbonated hydroxyapatite composition will depend upon the initial carbonate, $CO_3^{2-}$, concentration of the green composition and the density of the green composition. Generally, the higher the carbonate concentration of the green composition and the higher the density of the green composition, the lower is the temperature at which substantially complete densification will occur.

It will be appreciated that the use of relatively low sintering temperatures provides clear economic advantages. It is thus preferred to sinter the green compositions at temperatures towards the lower end of the above stated temperature range, preferably at temperatures within the range of from 750° to 1150° C., the temperature being chosen according to the carbonate content and density of the green composition to provide the desired final composition. Furthermore, sintering at temperatures within this range is thought to produce a 100% dense material with minimum grain growth.

Although sintering at low temperatures is preferred for economic reasons, the method of the invention may be used at temperatures of up to 1450° C., for example at temperatures in the range of 1100° to 1300° C.

The green carbonated hydroxyapatite composition preferably has a green density of from 30 to 40% and a carbonate content of 3 to 10% by weight.

The carbonated hydroxyapatite compositions produced according to the method of the present invention preferably have a concentration of from 3 to 10% by weight of $CO_3^{2-}$ ions, with a concentration of 4 to 6% being preferred as equivalent to biological apatite.

The "wet" carbon dioxide atmosphere in which the sintering is carried out may be prepared by bubbling carbon dioxide through distilled water. The water content of the "wet" carbon dioxide produced by this method is within the above stated range and is preferably in the range of from 0.01 to 0.02 grams of water per liter of gas. The sintering time required to produce a fully dense composition may depend upon the temperature of sintering. Generally a sintering time of up to 24 hours, preferably 10 minutes to 4 hours, will be sufficient to produce a composition which is at least 95% dense.

The sintering method of the present invention is carried out at substantially atmospheric pressure, i.e. no imposed pressure is used during the sintering, although pressures slightly higher than atmospheric may be produced by the particular configuration of the furnace used.

The compositions produced according to the method of the present invention are at least 95% dense, preferably from 98 to 100% dense. The compositions which are fully dense or substantially fully dense are translucent.

The preparation of the green carbonated hydroxyapatite composition may be carried out according to techniques known in the art. For example, calcium nitrate and tri-ammonium orthophosphate may be reacted in aqueous medium with varying concentrations of sodium bicarbonate made basic (above pH9) by the addition of ammonium hydroxide at 35° C. to produce predominantly B type apatites containing up to about 8 wt % carbonate. Another method involves the addition of calcium acetate to a mixture of sodium monohydrogen phosphate and sodium bicarbonate. Furthermore, predominantly type B carbonated apatites may be prepared by the soaking of stoichiometric hydroxyapatite in highly carbonated water for more than one month yielding carbonate contents of up to about 5.5% by weight. It will be appreciated that there are many other possible methods for the production of the carbonated hydroxyapatite, all involving the combination of calcium, phosphate and carbonate or bicarbonate ions in basic conditions.

The carbonated hydroxyapatite produced according to the above described techniques is filtered preferably to produce a filter cake which is then dried to produce a green compact. It is preferably advantageous if the filter cakes are dried slowly whilst eliminating air currents across the surface thereof for example at a drying rate of less than 0.2 g per minute removal of solvent. This can be achieved by wrapping the filter cakes in a thick layer of cotton wool which reduces the drying rate, eliminates air currents across the surfaces and prevents the creation of frictional stresses upon shrinkage as the cotton wool is free to move with the filter cake.

The present invention will be further described with reference to the following non-limiting Examples.

In these Examples the measurement of green density was estimated to be accurate to within ±3%. The measurement of $CO_3^{2-}$ content was estimated to be accurate only to ±25% at levels of up to 5 wt % and accurate only to ±20% at levels of above 5 wt %.

EXAMPLE 1

A carbonated hydroxyapatite was produced according to the following method. A 0.13 solution of tri-ammonium orthophosphate at pH $\geq 9$ was dripped into a continously stirred 0.21M solution of calcium nitrate 4-hydrate over a period of approximately two hours at a temperature of 3° C. The solution was filtered to remove insoluble impurities. Sodium bicarbonate (0.08M) was added to the phosphate solution and the resulting precipitate aged for 24 hours and then filtered in a Buchner Funnel equipped with a removable bottom, boiled in distilled water and filtered again. The removable bottom of the Buchner funnel enabled the filter cake to be removed without exerting any stresses on it. During drying the compact was wrapped in a thick layer of cotton wool, which reduced the drying rate, (thermal gradients), eliminated air currents across the surfaces and prevented the creation of frictional stresses upon shrinkage as the cotton wool was free to move with the sample. Once the compact had started to harden, it was suspended in a clamp to prevent uneven drying rates.

The green compacts of carbonated hydroxyapatite produced by this method contained approximately 4.0% by weight of $CO_3^{2-}$ ions measured using a Perkin Elmer 2400 CHN Analyser and had a green density of 39%.

Green compacts were sintered in a Carbolite 1600 STF tube furnace at a temperature of 1250° C. in the following four atmospheres.

i) air;

ii) 99.995% carbon dioxide;

"wet" carbon dioxide containing approximately 0.015 grams per liter of water; and iv) "wet" air containing approximately 0.015 grams per liter of water.

The compacts were heated at a rate of 2.5° C. per minute with a dwell time of four hours in all cases. The samples were mounted in resin, polished and etched and examined using scanning electron microscopy. The electron micrographs are shown in FIG. 1.

Carbonated hydroxyapatite sintered in dry carbon dioxide appeared to retain about 10% porosity, whilst the sample sintered in "wet" carbon dioxide was substantially fully dense. Carbonated hydroxyapatite sintered in "wet" air and in air only were fairly similar with intergranular porosity. The carbonated hydroxyapatite sintered in "wet" carbon dioxide was translucent, whereas all of the other sintering conditions produced white opaque bodies.

EXAMPLE 2

The procedure of Example 1 was repeated but the green components were sintered at a temperature of 1150° for 4 hours in the following three atmospheres:

i) air;

ii) 99.95% carbon dioxide; and iii) "wet" carbon dioxide containing approximately 0.015 grams per liter of water.

Figure 1A:
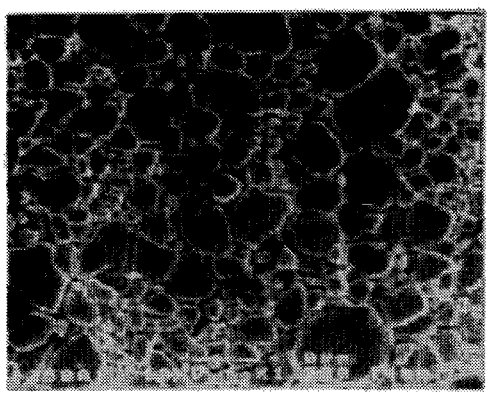
FIG. 1A is an electron micrograph of a carbonate apatite microstructure of the composition of Example 1 after sintering at 1250° C. for 4 hours in air.
Figure 1B:
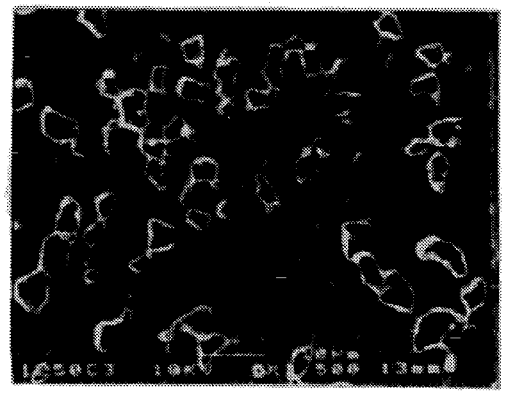
FIG. 1B is an electron micrograph of a carbonate apatite microstructure of the composition of Example 1 after sintering for 4 hours in carbon dioxide.
Figure 1C:
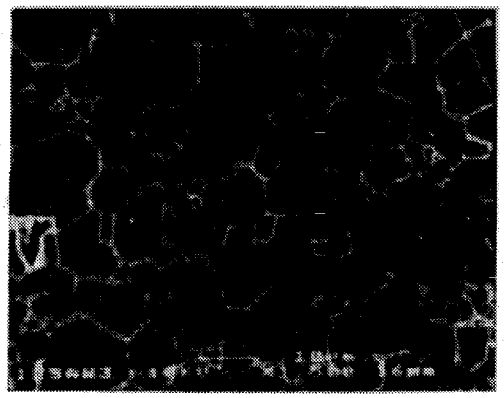
FIG. 1C is an electron micrograph of a carbonate apatite microstructure of the composition of Example 1 after sintering at 1250° C. for 4 hours in wet air.
Figure 1D:
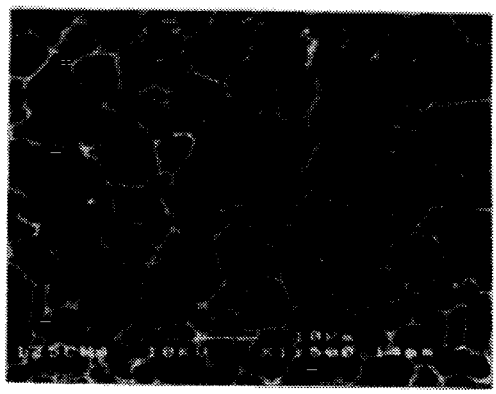
FIG. 1D is an electron micrograph of a carbonate apatite microstructure of the composition of Example 1 after sintering at 1250° C. for 4 hours in wet carbon dioxide.
Figure 2:
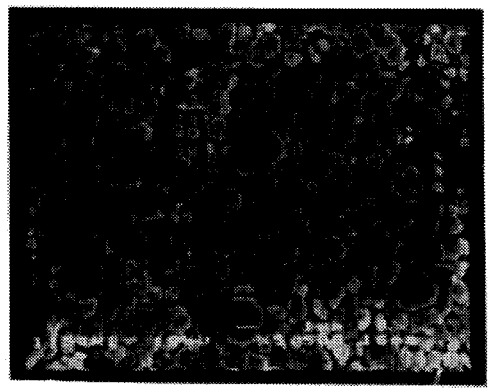
FIG. 2 is an electron micrograph of the microstructure of the composition of Example 2 after sintering at 1150° C. for 4 hours in wet carbon dioxide.
Figure 3:
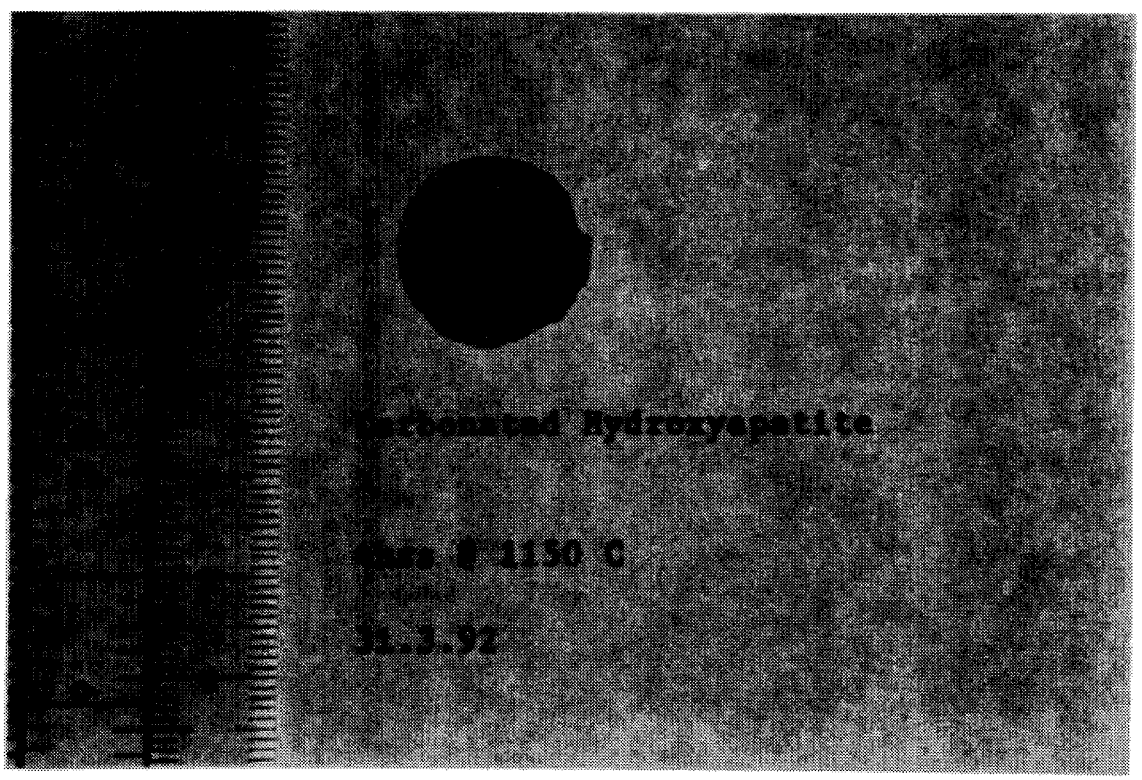
FIG. 3 is a photograph illustrating the translucency of the composition of Example 2 after sintering at 1150° C. for 4 hours in wet carbon dioxide.

An electron micrograph of the microstructure obtained in "wet" carbon dioxide is shown in FIG. 2. The translucency of this sample is shown in FIG. 3. The densities of the sintered products obtained in Examples 1 and 2 are given below in Table 1.

TABLE 1

| Densities of sintered samples (units $Mgm^{-3} \pm 0.005$) | | | | |
| --- | --- | --- | --- | --- |
| Temperature/ °C. | Air | Dry $CO_2$ | "Wet" $CO_2$ | "Wet" air |
| 1150 | 3.12 | 3.06 | 3.13 | |
| 1250 | 3.12 | 3.07 | 3.13 | 3.14 |

(The theoretical density of hydroxyapatite is approximately 3.14)

EXAMPLE 3

A green carbonated hydroxyapatite composition containing approximately 7.8% by weight of $CO_3^{2-}$ ions measured using a CEC Control Equipment Corporation Model 240 XA CHN Analyser and having a green density of 32% was sintered according to the procedure of Example 1 in "wet" carbon dioxide containing approximately 0.015 grams per liter of water at temperatures of from 700° to 1300° C., with a dwell time of 4 hours. At temperatures in the range of from 950° to 175° C. substantially complete densification of the samples was obtained and the samples were translucent.

EXAMPLE 4

A green carbonated hydroxyapatite composition containing approximately 11.5% by weight of $CO_3^{2-}$ ions measured using a Perkin Elmer 2400 CHN Analyser and having a green density of 36% was sintered according to the procedure of Example 1 in "wet" carbon dioxide containing approximately 0.015 grams per liter of water at temperatures of from 700° to 1100° C., with a dwell time of 4 hours.

At temperatures in the range of from 750° to 900° C. substantially complete densification of the samples was obtained and the samples were translucent.

EXAMPLE 5

A green carbonated hydroxyapatite composition containing approximately 5.8% by weight of $CO_3^{2-}$ ions measured using a CEC Control Equipment Coporation Model 240 XA CHN Analyser and having a green density of 35% was sintered according to the procedure of Example 1 in "wet" carbon dioxide containing approximately 0.015 grams per liter of water at temperatures of from 700° to 1250° C., with a dwell time of 4 hours.

At temperature in the range of from 750° to 1050° C. substantially complete densification of the samples was obtained and the samples were translucent.

We claim:

1. A method for the preparation of a carbonated hydroxyapatite composition which has a density of at least 95% of the theoretical density, which method comprises sintering at substantially atmosphere pressure a dry green carbonated hydroxyapatite compact which contains up to 20% by weight of $CO_3$ ions but which does not contain any binder and which has a green density of from 25 to 60% of the theoretical density at a temperature in the range of from 750° to 1450° C. in carbon dioxide containing from 0.001 to 0.10 grams of water per liter of gas, the sintering temperature being selected within the above range and the green compact being sintered for a period of time sufficient to cause the green compact to densify to at least 95% of the theoretical density.

2. Method as claimed in claim 1 wherein the green composition has a density of 30 to 40% of the theoretical density.

3. Method as claimed in claim 1 wherein the sintering temperature is in the range of from 750° to 1150° C.

4. Method as claimed in claim 1 wherein the carbon dioxide contains from 0.01 to 0.02 grams of water per liter of gas.

5. Method as claimed in claim 1 wherein the sintering is carried out for a period of time of up to 24 hours.

6. Method as claimed in claim 5 wherein the sintering is carried out for a period of time of up to 4 hours.

7. Method as claimed in claim 1 wherein the green carbonated hydroxyapatite composition has a carbonate content of from 3 to 10% by weight.

8. Method as claimed in claim 1 wherein the carbonated hydroxyapatite composition comprises from 4 to 6% by weight of $CO_3^{2-}$ ions.

9. Method as claimed in claim 1 wherein the carbonated hydroxyapatite has a density of from 98% to 100% of the theoretical density.

10. Method as claimed in claim 9 wherein the carbonated hydroxyapatite is translucent.

11. A method for the preparation of a carbonated hydroxyapatite composition which has a density of at least 95% of the theoretical density, which method comprises sintering at substantially atmosphere pressure a dry green carbonated hydroxyapatite compact which contains up to 20% by weight of $CO_3$ ions but which does not contain any binder at a temperature in the range of from 1000° to 1450° C. in carbon dioxide containing from 0.001 to 0.10 grams of water per liter of gas, for a period of time sufficient to cause the green compact to densify to at least 95% of the theoretical density.

12. Method as claimed in claim 11 wherein the sintering temperature is in the range of from 1100° to 1300° C.

13. Method as claimed in claim 11 wherein the carbon dioxide contains from 0.01 to 0.02 grams of water per liter of gas.

14. Method as claimed in claim 11 wherein the carbonated hydroxyapatite composition comprises from 4 to 6% by weight of $CO_3^{2-}$ ions.

* * * * *